United States Patent [19]

Schwamborn et al.

[11] Patent Number: 4,627,872
[45] Date of Patent: Dec. 9, 1986

[54] 2,4-DIAMINOPYRIMIDINES

[75] Inventors: Michael Schwamborn, Cologne; Engelbert Kühle, Bergisch-Gladbach; Ludwig Eue, Leverkusen; Robert R. Schmidt, Bergisch-Gladbach; Hans-Joachim Santel, Cologne, all of Fed. Rep. of Germany

[73] Assignee: Bayer Aktiengesellschaft, Leverkusen, Fed. Rep. of Germany

[21] Appl. No.: 806,053

[22] Filed: Dec. 5, 1985

[30] Foreign Application Priority Data

Dec. 12, 1984 [DE] Fed. Rep. of Germany ....... 3445293

[51] Int. Cl.$^4$ .................... A01N 43/54; C07D 239/48
[52] U.S. Cl. .......................... 71/92; 71/72; 71/74; 544/319; 544/320; 544/323; 544/326; 544/327; 544/332; 544/334
[58] Field of Search ...................... 544/323, 320; 71/92

[56] References Cited

U.S. PATENT DOCUMENTS 3,892,554  7/1975  Schneider ........................... 544/323
4,559,345 12/1985  Gomarasca et al. ................ 544/323

Primary Examiner—Richard L. Raymond
Assistant Examiner—James H. Turnipseed
Attorney, Agent, or Firm—Sprung, Horn, Kramer & Woods

[57] ABSTRACT

New herbicidally active 2,4-diamino pyrimidines of the formula

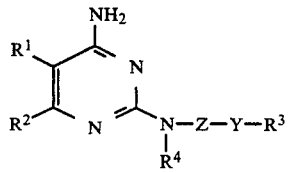

wherein $R^1$ is hydrogen or halogen, $R^2$ is an optionally halogen-substituted alkyl or is halogen or alkoxy; $R^3$ is hydrogen or alkyl; Y is oxygen or sulfur; and Z is a branched or unbranched alkylene.

6 Claims, No Drawings

2,4-DIAMINOPYRIMIDINES

The present invention relates to new 2,4-diaminopyrimidines, processes for their preparation and their use as plant protection agents, especially as herbicides.

It is already known that certain 2,4-diaminopyrimidines, for example 2,4-biscyclopropylamino-5,6-dichloropyrimidine, can be employed as herbicides (see DE-OS (German Published Specification) No. 2,006,145 and DE-OS (German Published Specification) No. 2,630,140). However, when low amounts are used, their action against various harmful plants is not satisfactory.

There have now been found new 2,4-diaminopyrimidines of the general formula (I)

in which
$R^1$ represents hydrogen or halogen,
$R^2$ represents optionally halogen-substituted alkyl, or represents halogen or alkoxy,
$R^3$ represents alkyl,
$R^4$ represents hydrogen or alkyl,
Y represents oxygen or sulfur and
Z represents branched or unbranched alkylene.

Further, it has been found that the pyrimidine derivatives of the general formula (I) are obtained when either
(A) halogenopyrimidines of the general formula (II)

(II)

in which
$R^1$ and $R^2$ have the abovementioned meaning and
X represents halogen (preferably fluorine or chlorine)
are first reacted with an amine of the formula (III)

(III)

wherein
$R^3$, $R^4$, Y and Z have the abovementioned meaning in the presence of an acid-binding agent and, if appropriate, in the presence of a diluent, to give a mixture of the isomeric pyrimidine derivatives of the general formula (IVa) and (IVb)

(IVa)       (IVb)

wherein
$R^1$, $R^2$, $R^3$, $R^4$, X, Y and Z have the abovementioned meaning,
(this being the 1st stage), and thereafter, when the two isomers have been separated, the pyrimidine derivatives of the formula (Iva) are reacted, in a further reaction step, with ammonia (V)

$$NH_3 \quad (V)$$

in the presence of an acid binding agent and, if appropriate, in the presence of a diluent, to give pyrimidine derivatives of the formula (I) (this being the 2nd stage), or (B) 4-aminopyrimidine derivatives of the general formula (VI)

(VI)

wherein
$R^1$, $R^2$ and X have the abovementioned meaning are reacted with an amine of the formula (III)—again uner the same reaction conditions as in the case of process (A)—to give pyrimidine derivatives of the formula (I)

(I)

wherein
$R^1$, $R^2$, $R^3$, $R^4$, Y and Z have the abovementioned meaning.

If $R^2$ represents halogen, this reaction gives a mixture of the isomeric pyrimidine derivatives of the general formula (I) and (Ia)

and (I)

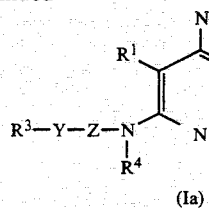

(Ia)

wherein

R¹, R², R³, R⁴, X, Y and Z have the abovementioned meaning from which the desired pyrimidine derivative of the general formula (I) is isolated.

Further, it has been found that the new pyrimidine derivatives of the general formula (I) exhibit powerful herbicidal properties.

The new pyrimidine derivatives according to the invention, of the formula (I), are structurally distinguished from the previously known pyrimidines especially in that the 2-amino group contains a straight-chain or branched alkyl chain interrupted by oxygen or sulfur and that an unsubstituted amino group is present in the 4-position.

Surprisingly, the active compounds according to the invention, of the formula (I), while having the same toleration by crops are distinctly more active than the previously known pyrimidine derivatives, such as, for example, 2,4-biscyclopropylamino-5,6-dichloropyrimidine (known from DE-OS (German Published Specification) No. 2,630,140).

Among the pyrimidine derivatives according to the invention, of the formula (I), those are preferred in which R¹ represents hydrogen, chlorine or fluorine, R² represents chlorine, fluorine, alkoxy with 1-6 C atoms or alkyl with 1-6 C atoms which is optionally substituted by chlorine and/or fluorine, R³ represents alkyl with 1-6 C atoms, R⁴ represents hydrogen or alkyl with 1-6 C atoms, Y represents oxygen or sulfur and Z represents a branched or unbranched alkylene group with 2 to 10 C atoms.

Among this group of substances, those compounds of the formula (I) are particularly preferred in which R¹ represents hydrogen, chlorine or fluorine, R² represents chlorine, fluorine, alkoxy with 1-3 C atoms or alkyl with 1 or 2 C atoms which is optionally substituted by chlorine and/or fluorine, R³ represents alkyl with 1-4 C atoms, R⁴ represents hydrogen or alkyl with 1-4 C atoms, Y represents oxygen or sulfur and Z represents a branched or unbranched alkylene group with 2-7 C atoms.

If, for example, in process (A) 2,4,6-trichloropyrimidine and 3-methoxypropylamine are used as starting materials and the 4,6-dichloro-2-(3-methoxypropylamino)pyrimidine thereby formed is reacted further with ammonia, the course of the reaction can be represented, in summary, by the following set of formulae:

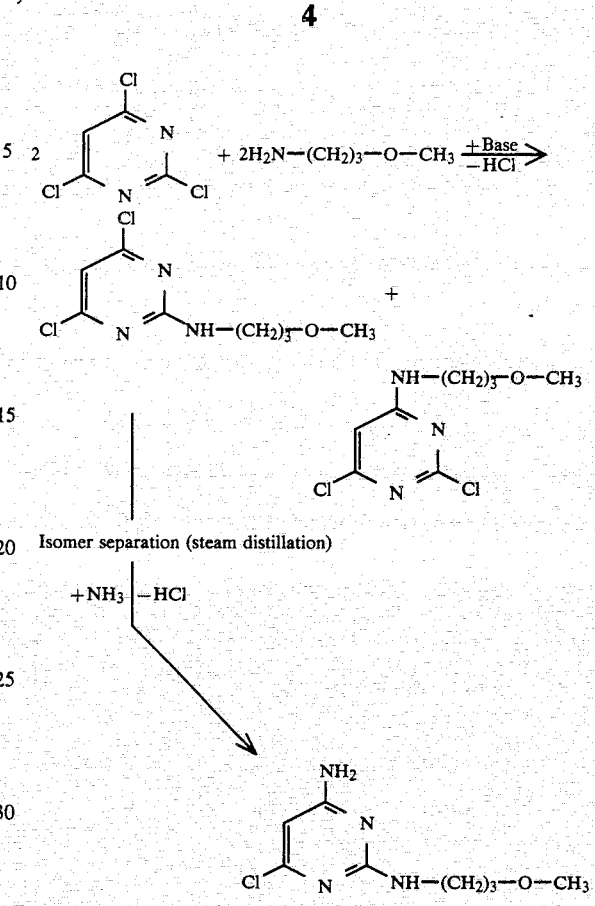

If, for example, in process (B) 4-amino-2,5,6-trichloropyrimidine is used as the starting material and is reacted with 3-methoxypropylamine, the course of the reaction can be represented, in summary, by the following set of formulae:

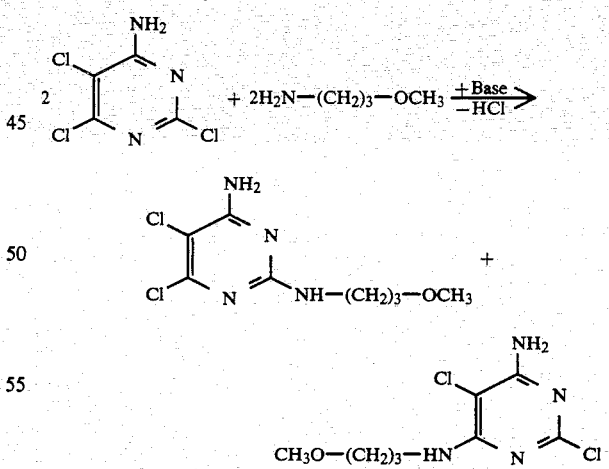

ISOLATION BY ISOMER SEPARATION (CRYSTALLISATION)

The formula (II) provides a general definition of the halogenopyrimidines used as starting materials. In this formula, R¹ and R² preferably, or particularly preferentially, represent those radicals which have already been mentioned as being preferred or particularly preferred for these substituents in the description of the compounds according to the invention, of the formula (I), and X represents chlorine or fluorine. The halogenopyrimidines of the formula (II) are in some cases known, or can be prepared in accordance with known processes (See the examples).

The formula (III) provides a general definition of the amines furthermore used as starting materials. In this formula, $R^3$, $R^4$, Y and Z preferably, or particularly preferentially, represent those radicals which have already been mentioned as being preferred or particularly preferred for these substituents in the description of the compounds according to the invention, of the formula (I). The amines of the formula (III) are known or can be prepared in accordance with known processes, analogously to the known compounds (see, for example, Houben-Weyl, Methoden der organischen Chemie (Methods of Organic Chemistry), Volume XI/1, page 548, page 561 et seq., 4th edition 1957; U.S. Pat. No. 2,764,615).

The formula (VI) provides a general definition of the 4-aminopyrimidine derivatives used as starting materials. In this formula, $R^1$ and $R^2$ preferably or particularly preferentially represent those radicals which have already been mentioned as being preferred or particularly preferred in the description of the compounds according to the invention, of the formula (I), and X represents chlorine or fluorine. The 4-aminopyrimidine derivatives of the formula (VI) are in some cases known or can be prepared in accordance with known processes (see the examples).

Possible diluents for the process variants (A) and (B) according to the invention are organic solvents as well as water. Preferred organic solvents are hydrocarbons, such as toluene, aliphatic ketones, such as acetone, methyl ethyl ketone and diethyl ketone, and cycloaliphatic ethers, such as tetrahydrofuran or dioxane. Mixtures of different organic solvents and mixtures of water-miscible organic solvents with water are also suitable for use as diluents.

The process variants (A) and (B) according to the invention can be carried out using acid acceptors. Particularly suitable as such are alkaline earth metal hydroxides and alkali metal hydroxides, such as calcium hydroxide, sodium hydroxide or potassium hydroxide, as well as ammonia and tertiary aliphatic amines, such as, for example, triethylamine, but also an excess of the amine starting product (III).

In the process according to the invention, the reaction temperatures can be varied within a substantial range. The first process stage in procedure (A) is in general carried out at temperatures of $-30°$ to $+150°$ C., preferably of $-20°$ to $+50°$ C.; the second process stage is in general carried out at 80° to 150° C., preferably 90° to 130° C. Procedure (B) is in general carried out at 80° to 150° C., preferably at 90° to 130° C.

The reaction is carried out in the pressure range of 1 to about 10 bar.

In carrying out process (A) according to the invention, 1 to 1.1 moles of amine of the formula III and 1 to 1.2 moles of acid acceptor are in general employed per mole of halogenopyrimidine of the formula (II) in the first stage, it being possible to use the amine (III) as acid acceptor. Preferably, the process is carried out using stoichiometric molar ratios. Analogous remarks apply to the second process stage as well as to process variant (B).

The isomer mixtures obtained in the two process variants can be separated in a simple manner, in accordance with the known methods, especially by recrystallisation, chromatography or steam distillation (see, for example, DE-OS (German Published Specification) No. 2,006,145, DE-OS (German Published Specification) No. 2,630,140 and European Pat. No. 0,114,575), so that the particular isomers desired can be isolated in a sufficiently pure form.

The active compounds according to the invention can be used as defoliants, desiccants, means of destroying broad-leaved plants and, in particular, as weedkillers. By weeds in the broadest sense there are to be understood all plants which grow in locations where they are undesired. Whether the compounds according to the invention act as total herbicides or selective herbicides essentially depends on the amount employed.

The active compounds according to the invention can be used, for example, on the following plants:

DICOTYLEDON WEEDS OF THE GENERA

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

DICOTYLEDON CULTURES OF THE GENERA

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

MONOCOTYLEDON WEEDS OF THE GENERA

Enchinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

MONOCOTYLEDON CULTURES OF THE GENERA

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds may be used, depending on the concentration, for the total combating of weeds, for example on industrial sites, rail tracks and paths and squares with and without tree growth. The compounds can also be used for combating weeds in perennial cultures, for example forestry, decorative woods, orchards, vineyards, citrus groves, nut, banana, coffee, tea, rubber, oil palm and cocoa plantations, soft fruit plantings and hopfields, and for the selective combating of weeds in annual cultures.

The active compounds according to the invention can—especially in the post-emergence process—be employed for the selective combating of weeds in monocotyledon cultures, for example in maize, cereals and rice, and dicotyledon cultures, for example in cotton and soya. The new active compounds, while possessing the same toleration both for maize, cereals and rice and for cotton and soya, are distinctly more active than the previously known compound 2,4-biscyclopropylamino-5,6-dichloropyrimidine.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound and very fine capsules in polymeric substances.

These formulations are produced in known manner, for example by mixing the active compounds with extenders, that is, liquid solvents, and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable, for example, ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable, for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations, as well as natural phospholipids, such as kephalins and lecithins, and synthetic phospholipids. Mineral oils and vegetable oils can be further additives.

It is possible to use colorants such as inorganic pigments, for example iron oxide, titanium oxide and Prussian Blue, and organic dyestuffs, such as alizarin dyestuffs, azo dyestuffs and phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active substances according to the invention, as such or in the form of their formulations, can also be employed for weed combating as mixtures with known herbicides, finished formulations or tank mixing being possible.

In herbicidal use, possible partners in the mixture are ureas (for example methabenzthiazurone); diphenyl ethers, acetanilides (for example alachlor and metolachlor); phenoxyalkanecarboxylic acids (for example 2,4-D, 2,4-DP, MCPA, MCPP and their derivatives); aryloxy- and hetaryloxyphenoxy-propionic acid (for example trimethylsilylmethyl-2-[4-(3,5-dichloro-2-pyridyloxy)-phenoxy]-propionate; (2,2-diethoxy)-ethyl 2-[4-(3,5-dichloro-2-pyridyloxy)-phenoxy]propionate, (2-benzyloxy)-ethyl 2-[4-(3,5-dichloro-2-pyridyloxy)-phenoxy]-propionate; triazines (for example atrazine and simazine); triazinones (for example metribuzine and 4-amino-6-tert.-butyl-3-ethylthio-1,2,4-triazin-5(4H)-one); triazinediones (for example ametridione); cyclohexanediones (for example sethoxydim); benzonitriles (for example Ioxynil) and bentazone.

Mixtures with other known active compounds, such as fungicides, insecticides, acaricides, nematicides, bird repellants, plant nutrients and agents which improve soil structure are also possible.

The active substances can be employed as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound employed can vary within substantial ranges. It depends essentially on the nature of the desired effect. In general the amounts employed are between 0.01 and 15 kg of active compound per ha, preferably between 0.05 and 10 kg per ha.

The preparation and use of the active compounds according to the invention is shown in the examples which follow.

PREPARATION EXAMPLES

Example 1

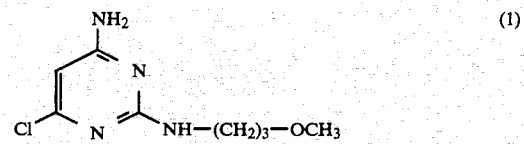
(1)

4-Amino-6-chloro-2-(3-methoxypropylamino)-pyrimidine according to process (A)

(a)

4,6-Dichloro-2-(3-methoxypropylamino)-pyrimidine/1st stage 48 g (0.54 mole) of 3-methoxypropylamine are added dropwise to 50 g (0.27 mole) of 2,4,6-trichloropyrimidine, dissolved in 300 ml of tetrahydrofuran, at −30° C. After the reaction mixture has thawed to room temperature and been stirred for a further six hours, it is poured into ice water and extracted with methylene chloride, the extract is dried over sodium sulphate and the solvent is removed. The resulting residue is subjected to steam distillation in the course of which 10.6 g (16.6% of theory) of the desired pyrimidine pass over as a solid, melting point 48° C.

(b)
4-Amino-6-chloro-2-(3-methoxypropylamino)-pyrimidine/2nd stage 10 g (0.042 mole) of 4,6-dichloro-2-(3-methoxypropylamino)-pyrimidine are dissolved in 100 ml of dioxane and 60 ml of aqueous ammonia solution are added. After the reaction mixture has been heated to the boil for four hours, it is mixed with 1 liter of ice water and extracted with methylene chloride. The extract is dried over sodium sulphate and concentrated, and the residue which remains is boiled up with white spirit, filtered off and dried. 5.6 g (61.6% of theory) of the desired pyrimidine, melting point 141° C., are obtained.

EXAMPLE 2

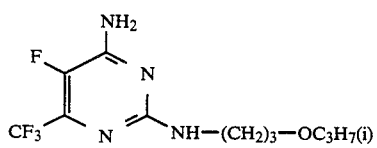

4-Amino-2-(3-isopropoxypropylamino)-5-fluoro-6-trifluoromethylpyrimidine according to process (B)

5 g (0.025 mole) of 4-amino-2,5-difluoro-6-trifluoromethylpyrimidine are dissolved in 150 ml of dioxane. 2.9 g (0.025 mole) of 3-isopropoxypropylamine and 2.5 g (0.025 mole) of triethylamine are added dropwise thereto and the reaction mixture is heated to the boil for five hours. It is cooled and stirred into ice water, and the resulting solid is filtered off, dried and recrystallised from white spirit. 4 g (54% of theory) of the desired pyrimidine, melting point 87° C., are obtained.

Example 3

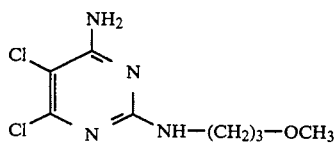

4-Amino-2-(3-methoxypropylamino)-5,6-dichloropyrimidine according to process (B)

1,850 g (9.31 moles) of 4-amino-2,5,6-trichloropyrimidine are dissolved in 4 liters of tetrahydrofuran. 1,659 g (18.62 moles) of 3-methoxypropylamine are added dropwise thereto over a period of 6 hours. The reaction mixture is heated for five hours at the boil, cooled and stirred into 20 liters of water. The resulting solid is filtered off, dried, stirred with 7 liters of methylene chloride and again filtered off. After the solid thus obtained has been twice recrystallised from toluene, 743 g (31.8% of theory) of the desired pyrimidine, melting point 114° C., are obtained.

Example 4

4-Amino-2-(3-methoxy-1-methylpropylamino)-5,6-dichloropyrimidine according to process (B)

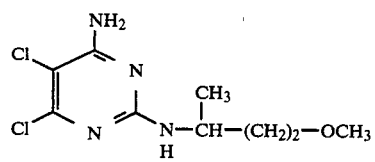

3.4 g (0.033 mole) of 3-methoxy-1-methylpropylamine and 3.3 g (0.033 mole) of triethylamine are successively added dropwise to a solution of 6.5 g (0.033 mole) of 4-amino-2,5,6-trichloropyrimidine in 200 ml of toluene and the mixture is heated to the boil for five hours. When it has cooled, the reaction mixture is washed with water and the organic phase is dried over sodium sulphate and concentrated. The crude product thus obtained is purified by chromatography over silica gel (length of column: 80 cm, diameter: 5 cm), using ethyl acetate and petroleum ether (1:1). In addition to 4-amino-6-(3-methoxy-1-methylpropylamino)-2,5-dichloropyrimidine (1st fraction, melting point 62° C.), 1.5 g (17.2% of theory) (2nd fraction, melting point 96° C.) of the desired pyrimidine are obtained.

The pyrimidine derivatives of the general formula (I)

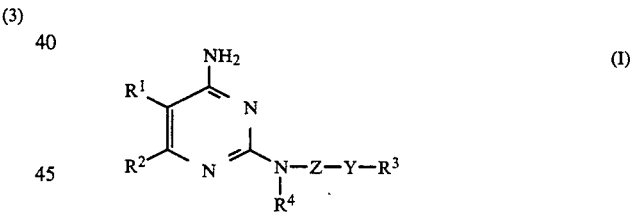

mentioned in Table 1 below can be prepared analogously.

TABLE 1

| Example No. | $R^1$ | $R^2$ | $R^3$ | $R^4$ | Z | Y | Physical constants |
| --- | --- | --- | --- | --- | --- | --- | --- |
| 5 | Cl | CH$_3$ | C$_2$H$_5$ | H | —(CH$_2$)$_3$— | O | melting point 84° C. |
| 6 | Cl | CH$_3$ | C$_3$H$_7$(i) | H | —(CH$_2$)$_3$— | O | oil |
| 7 | Cl | CH$_3$ | CH$_3$ | H | —CH—(CH$_2$)$_2$—<br>$\mid$<br>CH$_3$ | O | melting point 68–70° C. |
| 8 | Cl | Cl | C$_2$H$_5$ | H | —(CH$_2$)$_3$— | O | isomer mixture melting point 67–70° C. |
| 9 | Cl | Cl | C$_3$H$_7$(i) | H | —(CH$_2$)$_3$— | O | isomer mixture melting point 44–52° C. |
| 10 | Cl | CH$_3$ | CH$_3$ | H | —(CH$_2$)$_3$— | O | melting point 66–68° C. |
| 11 | Cl | Cl | C$_2$H$_5$ | H | —CH—(CH$_2$)$_2$—<br>$\mid$<br>CH$_3$ | O | |

TABLE 1-continued

| Example No. | $R^1$ | $R^2$ | $R^3$ | $R^4$ | Z | Y | Physical constants |
|---|---|---|---|---|---|---|---|
| 12 | Cl | Cl | $C_3H_7(i)$ | H | $-CH(CH_3)-(CH_2)_2-$ | O | |
| 13 | Cl | Cl | $CH_3$ | H | $-CH(CH_3)-CH_2-$ | O | |
| 14 | Cl | Cl | $C_2H_5$ | H | $-CH(CH_3)-CH_2-$ | O | |
| 15 | Cl | Cl | $C_3H_7$ | H | $-CH(CH_3)-CH_2-$ | O | |
| 16 | Cl | Cl | $CH_3$ | $CH_3$ | $-(CH_2)_2-$ | O | |
| 17 | Cl | Cl | $CH_3$ | $C_2H_5$ | $-(CH_2)_2-$ | O | |
| 18 | F | F | $CH_3$ | H | $-CH(CH_3)-(CH_2)_2-$ | O | |
| 19 | F | $OC_2H_5$ | $CH_3$ | H | $-CH(CH_3)-(CH_2)_2-$ | O | |
| 20 | Cl | Cl | $CH_3$ | H | $-CH(CH_3)-(CH_2)_2-$ | S | |
| 21 | F | $CF_3$ | $CH_3$ | H | $-(CH_2)_3-$ | O | melting point 98° C. |
| 22 | F | $CF_3$ | $CH_3$ | H | $-CH(CH_3)-(CH_2)_2-$ | O | melting point 95–97° C. |
| 23 | F | $CF_3$ | $C_2H_5$ | H | $-(CH_2)_3-$ | O | |
| 24 | Cl | $CHCl_2$ | $CH_3$ | H | $-(CH_2)_3-$ | O | melting point 112–114° C. |
| 25 | Cl | $CHCl_2$ | $C_2H_5$ | H | $-(CH_2)_3-$ | O | |
| 26 | Cl | $CHCl_2$ | $C_3H_7(i)$ | H | $-(CH_2)_3-$ | O | melting point 80° C. |
| 27 | Cl | $CHCl_2$ | $CH_3$ | H | $-CH(CH_3)-(CH_2)_2-$ | O | |
| 28 | Cl | $CF_3$ | $CH_3$ | H | $-(CH_2)_3-$ | O | |
| 29 | Cl | $CF_3$ | $C_2H_5$ | H | $-(CH_2)_3-$ | O | |
| 30 | Cl | $CF_3$ | $C_3H_7(i)$ | H | $-(CH_2)_3-$ | O | |
| 31 | Cl | $CF_3$ | $CH_3$ | H | $-CH(CH_3)-(CH_2)_2-$ | O | |
| 32 | Cl | Cl | $CH_3$ | H | $-CH_2-CH(C_3H_7(i))-CH_2-$ | O | $n_D^{20}$: 1.5478 |
| 33 | Cl | Cl | $CH_3$ | H | $-CH_2-CH(CH_3)-CH_2-$ | O | Fp.: 86° C. |
| 34 | Cl | Cl | $CH_3$ | H | $-(CH_2)_3-$ | S | Fp.: 88° C. |
| 35 | Cl | Cl | $-(CH_2)_4CH_3$ | H | $-(CH_2)_3-$ | O | Fp.: 37° C. |
| 36 | Cl | Cl | $-(CH_2)_5CH_3$ | H | $-(CH_2)_3-$ | O | Fp.: 45° C. |
| 37 | Cl | Cl | $CH_3$ | H | $-(CH_2)_3-CH(CH_3)-$ | O | $n_D^{20}$: 1.5680 |
| 38 | Cl | Cl | $-CH_2CH(CH_3)_2$ | H | $-(CH_2)_3-$ | O | Fp.: 72° C. |
| 39 | Cl | Cl | $-C_4H_9(t)$ | H | $-(CH_2)_3-$ | O | Fp.: 80° C. |
| 40 | Cl | Cl | $CH_3$ | $CH_3$ | $-(CH_2)_2-$ | S | Fp.: 108° C. |

TABLE 1-continued

| Example No. | R¹ | R² | R³ | R⁴ | Z | Y | Physical constants |
|---|---|---|---|---|---|---|---|
| 41 | Cl | Cl | $CH_3$ | H | $-\underset{\underset{CH_3}{\vert}}{\overset{\overset{CH_3}{\vert}}{C}}-CH_2-$ | O | |
| 42 | Cl | $-CH_2Cl$ | $CH_3$ | H | $-\underset{\underset{CH_3}{\vert}}{CH}-(CH_2)_2-$ | O | Fp.: 110° C |

STARTING MATERIALS

The halogenopyrimidines of the formulae (II-1) to (II-8), used as starting materials, and their preparation, are known; alternatively, the compounds can be obtained in an analogous manner to the processes described for the known compounds:

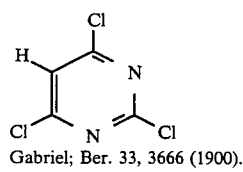
(II-1)
Gabriel; Ber. 33, 3666 (1900).

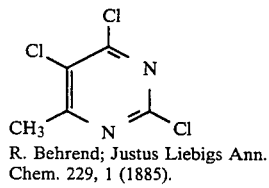
(II-2)
R. Behrend; Justus Liebigs Ann. Chem. 229, 1 (1885).

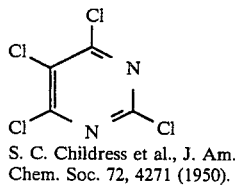
(II-3)
S. C. Childress et al., J. Am. Chem. Soc. 72, 4271 (1950).

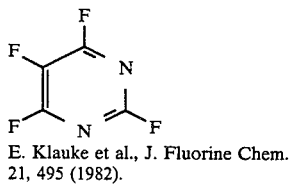
(II-4)
E. Klauke et al., J. Fluorine Chem. 21, 495 (1982).

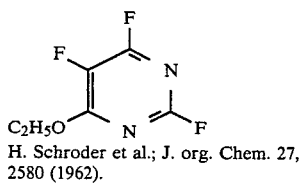
(II-5)
H. Schroder et al.; J. org. Chem. 27, 2580 (1962).

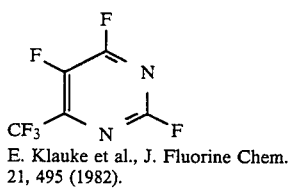
(II-6)
E. Klauke et al., J. Fluorine Chem. 21, 495 (1982).

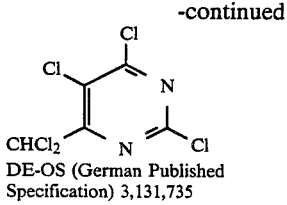
(II-7)
DE-OS (German Published Specification) 3,131,735

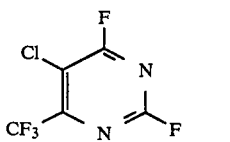
(II-8)
E. Klauke et al., J. Fluorine Chem. 21, 495 (1982).

The aminopyrimidines of the formula (VI-1) to (VI-5), used as starting materials, and their preparation, are known; alternatively, the compounds can be obtained in an analogous manner to the processes described for the known compounds:

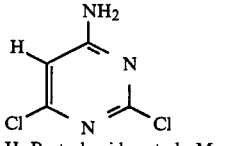
(VI-1)
H. Bretschneider et al.; Monatsh. Chem. 92, 128 (1961).

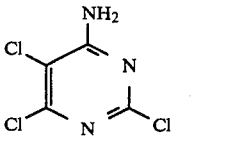
(VI-2)
S. C. Childress et al.; J. Am. Chem. Soc. 72, 4271 (1950).

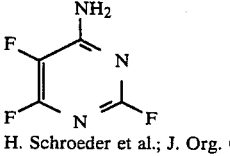
(VI-3)
H. Schroeder et al.; J. Org. Chem. 27, 2580 (1962).

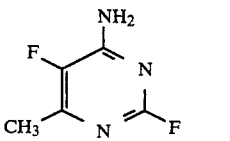
(VI-4)
E. Klauke et al.; J. Fluorine Chem. 21, 495 (1982).

-continued

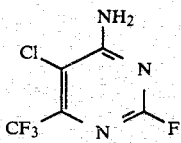
(VI-5)

E. Klauke et al.; J. Fluorine Chem. 21, 495 (1982).

USE EXAMPLES

In the use examples which follow the compound shown below is employed as the comparison substance:

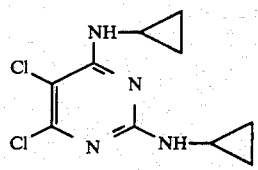
(VS-A)

(known from DE-OS (German Published Specification) No. 2,630,140, Example 12).

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior activity compound with the prior art is shown, for example, by the compounds according to the following preparation examples: (3) and (4).

What is claimed is:

1. A 2,4-Diaminopyrimidine of the formula

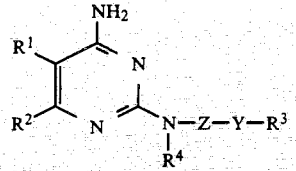

in which
R$^1$ represents hydrogen or halogen,
R$^2$ represents optionally halogen-substituted alkyl with 1–6 C atoms, or represents halogen or alkoxy with 1–6 C atoms,
R$^3$ represents alkyl with 1–6 C atoms,
R$^4$ represents hydrogen or alkyl with 1–6 C atoms,
Y represents oxygen or sulfur and
Z represents branched or unbranched alkylene with 2 to 10 C atoms.

2. A pyrimidine derivative according to claim 1, wherein
R$^1$ represents hydrogen, chlorine or fluorine
R$^2$ represents chlorine, fluorine, alkoxy with 1–3 C atoms or alkyl with 1 or 2 C atoms which is optionally substituted by chlorine and/or fluorine,
R$^3$ represents alkyl with 1–4 C atoms,
R$^4$ represents hydrogen or alkyl with 1–4 C atoms,
Y represents oxygen or sulfur and
Z represents a branched or unbranched alkylene group with 2 to 7 C atoms.

3. 4-Amino-2-(3-methoxypropylamino)-5,6-dichloropyrimidine of the formula

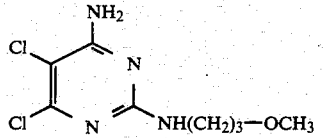

according to claim 1.

4. 4-Amino-2-(3-methoxy-1-methylpropylamino)-5,6-dichloropyrimidine of the formula

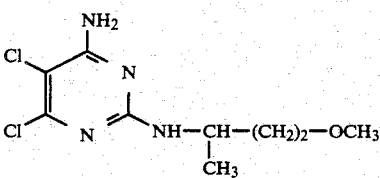

according to claim 1.

5. A herbicidal composition comprising a herbicidally effective amount of at least one 2,4-diaminopyrimidine of the formula according to claim 1 and an extender.

6. A method of combating weeds comprising applying to said weeds or to the location in which said weeds are growing a herbicidally effective amount of a 2-4-diaminopyrimidine of the formula according to claim 1.

* * * * *